United States Patent [19]

Kakinuma et al.

[11] 4,074,306
[45] Feb. 14, 1978

[54] ENDOSCOPE UTILIZING COLOR TELEVISION AND FIBER OPTICS TECHNIQUES

[75] Inventors: Yoshikazu Kakinuma, Hachioji; Tadashi Morokuma, Tokyo, both of Japan

[73] Assignee: Olympus Optical Co., Ltd., Tokyo, Japan

[21] Appl. No.: 708,262

[22] Filed: July 23, 1976

[51] Int. Cl.² ............................................... H04N 9/02
[52] U.S. Cl. ................................................... 358/1; 128/6; 350/96; 350/96.26; 358/98; 358/901
[58] Field of Search .................... 358/1, 42, 98, 901; 350/96 BC; 128/4, 6

[56] References Cited

U.S. PATENT DOCUMENTS 2,764,149  9/1956  Sheldon .............................. 358/1 X

OTHER PUBLICATIONS

Evening Star p. 1 Home Ed. May 2, 1967.

Primary Examiner—Robert L. Richardson
Attorney, Agent, or Firm—Haseltine, Lake & Waters

[57] ABSTRACT

An endoscope for displaying a color picture image of an object to be visualized in a hollow cavity is disclosed. The endoscope comprises a sheath to be inserted into said hollow cavity and an exterior circuit. The sheath includes a self-scanning type solid state image pick-up device, a bundle of lead wires composed of a lead wire for supplying a signal for operating said image pick-up device from said exterior circuit and a lead wire for leading out a picture image signal supplied from said image pick-up device toward said exterior circuit, and an illumination light transfer body for transferring a light for illuminating said object to be visualized from said exterior circuit. The exterior circuit includes a circuit for generating a signal for operating said solid state image pick-up device, an amplifier for amplifying said picture signal supplied from said image pick-up device, a color Braun tube for displaying a color picture image upon receipt of said image signal from said amplifier, a light source for emitting an illumination light on said illuminating light transfer body, means for decomposing light incident on said illumination light transfer body into color lights and a signal change-over circuit for changing over a signal supplied to said Braun tube by a synchronizing signal.

8 Claims, 36 Drawing Figures

FIG 24

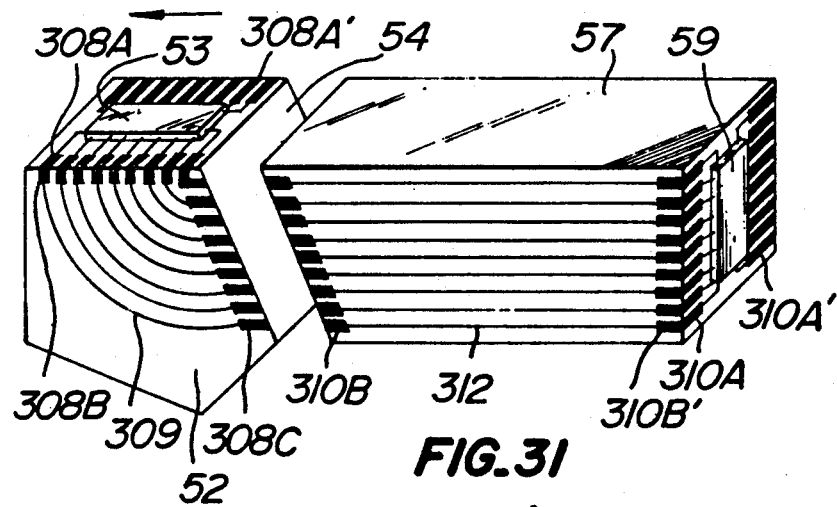
FIG._30
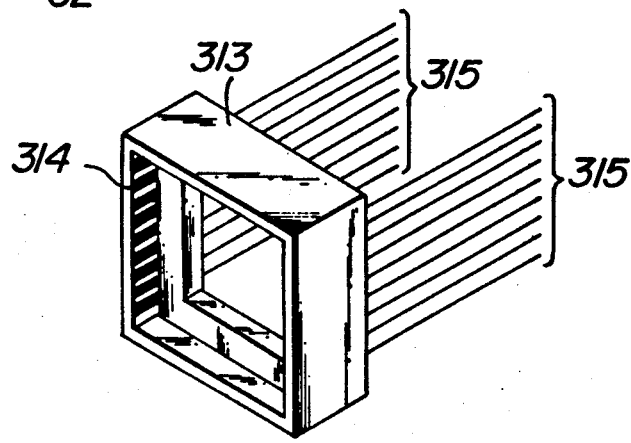
FIG._31

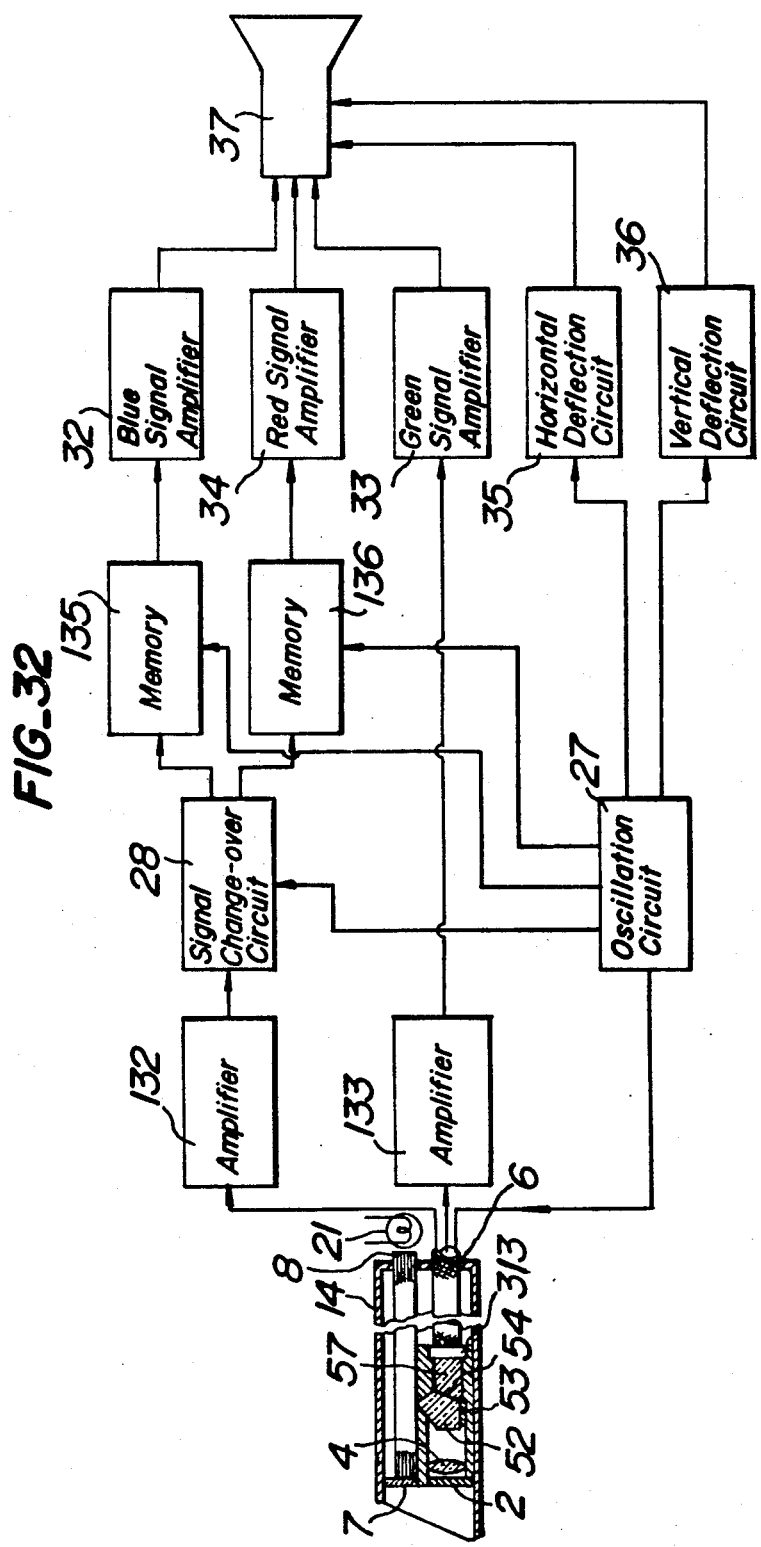

ENDOSCOPE UTILIZING COLOR TELEVISION AND FIBER OPTICS TECHNIQUES

This invention relates to an endoscope for visualizing the interior of a hollow organ or of a cavity in constitutional parts of a machine and simultaneously visualizing a color picture image by a number of persons.

In the endoscope, heretofore it has been the common practive to transmit a picture image of the hollow organ or cavity to be visualized (hereinafter will be called as hollow cavity) through an image guide to the exterior of the hollow cavity and obtain television picture signals by means of a vidicon tube, etc., which signals are subsequently displayed on a Braun tube for the purpose of simultaneously visualizing the color picture image by a number of persons. In addition, in the case of forming an easily discernible picture image by a picture image treatment such as a differentiation treatment or a filtration treatment so as to make the image contour distinguishable, use has also been made of a vidicon tube, etc. so as to transform the picture image into television picture signals and then the above mentioned treatment has been effected. The use of the vidicon tube provides the disadvantage that the endoscope becomes large in size and complex in construction and hence expensive and that various kinds of adjustments thereof are troublesome in operation. This disadvantage becomes more important if it is desired to display a color picture image.

In addition, the endoscope makes use of a rotary tricolor filter arranged between a light transfer body and a light source. The presence of the tricolor filter requires a mechanism for rotating the tricolor filter and a circuit for changing a signal to be supplied to a Braun tube into a signal synchronized with the rotation of the tricolor filter, and as a result, it is not always possible to provide an endoscope which is simple in construction and small in size. Moreover, that part of the endoscope which is inserted into the hollow cavity is provided therein with a bundle of lead wires connected to both the illumination light transfer body and a self-scanning type solid state image pick-up device. As a result, it is an inevitable consequence that part of the endoscope which is inserted into the hollow cavity becomes large in size.

The prior art endoscope has another disadvantage that if a light decomposition optical system or the solid state image pick-up device becomes damaged, it is troublesome to remove the solid state image pick-up device due to the presences of a number of long lead wires and mount the light decomposition optical system and the solid state image pick-up device in that part of the endoscope which is inserted into the hollow cavity.

In addition, in the endoscope, one solid state image pick-up device is supplied with a number of driving signals for the purpose of scanning an image of the object to be visualized, which is formed on the light receiving surface of the solid state image pick-up device, and hence picking up a picture image signal. In this case, there is a risk of the picture image being mixed with the driving signals. In order to prevent the picture image from being mixed with the driving signals, the endoscope is designed such that a compensation signal depending upon the driving signals is derived from the solid state image pick-up device and both the compensation signal and the picture signal are supplied through a bundle of lead wires to respective differential amplifiers arranged exterior of the hollow cavity, thereby compensating noises produced due to the driving signals and mixed into the picture signal and deriving a normal picture signal. In this case, if the bundle of lead wires for supplying the driving compensation signal and the picture signal to the respective differential amplifiers are formed by merely assembling together, noises produced due to the presence of devices arranged outside the hollow cavity or noises produced due to the driving compensation signals supplied to another solid state image pick-up device which is used in the case of displaying a color picture image are mixed into either one of the signal wires, and as a result, it is not always possible to derive a normal picture image. The noises are also displayed on the picture surface on the Braun tube, thereby degrading the quality of the displayed picture. In addition, the longer that part of the endoscope which is inserted into the hollow cavity is the more the mixing of various kinds of noises, thus resulting in a more significant deterioration of the quality of the displayed picture.

An object of the invention is to provide an endoscope which can display a color picture image of an object to be visualized without using a vidicon tube, which is small in size, simple in construction, easily operable, and less expensive.

Another object of the invention is to provide an endoscope which makes use of a light decomposing optical system composed of a pentaprism and a light transmission block and which can decompose a light reflected by an object to be visualized into three color signals in that part of the endoscope which is inserted into a hollow cavity.

A further object of the invention is to provide an endoscope which makes use of a delay circuit for delaying one of outputs from a solid state image pick-up device for one horizontal scanning period and a memory for reversing another output from another solid state image pick-up device during one horizontal scanning period.

A still further object of the invention is to provide an endoscope wich makes use of one package at least light output portion of which is transparent and which encloses therein a plurality of solid state light emitting chips adapted to emit blue, green and red lights, respectively, when supplied with electric current.

Another object of the invention is to provide an endoscope which makes use of one package at least light outlet portion of which is transparent and encloses therein a plurality of solid state light emitting chips adapted to emit blue, green and red lights, respectively, when supplied with electric current and a circuit for driving these light emitting chips.

Another object of the invention is to provide an endoscope comprising a light decomposition optical system composed of a light transmission prism and a light transmission block and including a number of signal transfer wires and connector contacts deposited on the light decomposition optical system and a receptacle including a number of contacts deposited therein and detachably connected to the connector contacts.

A further object of the invention is to provide an endoscope for visualizing the interior of a hollow cavity, which comprises a solid state image pick-up device mounted in that part of the endoscope which is inserted into the hollow cavity and a picture image signal wire and a driving compensation signal wire twisted together along their overall length, and which can derive a normal picture image signal without containing any external noise.

The invention will now be described in greater detail with reference to the accompanying drawings, wherein.

Figure 1:
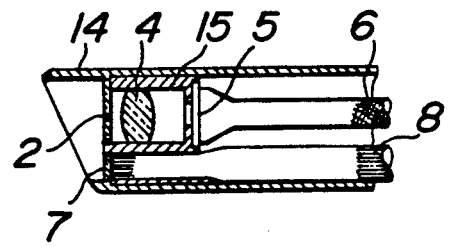
FIG. 1 is a partial sectional view showing one embodiment of that part of an endoscope according to the invention which is inserted into a hollow cavity and can display a color picture image.
Figure 3:
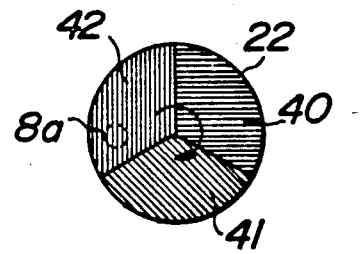
Figure 4:
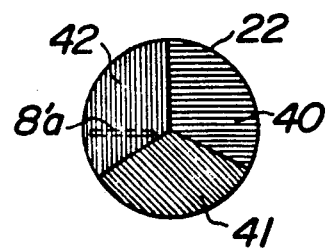
Figure 5:
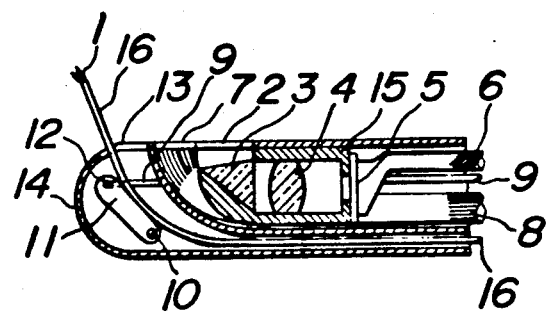
Figure 2:
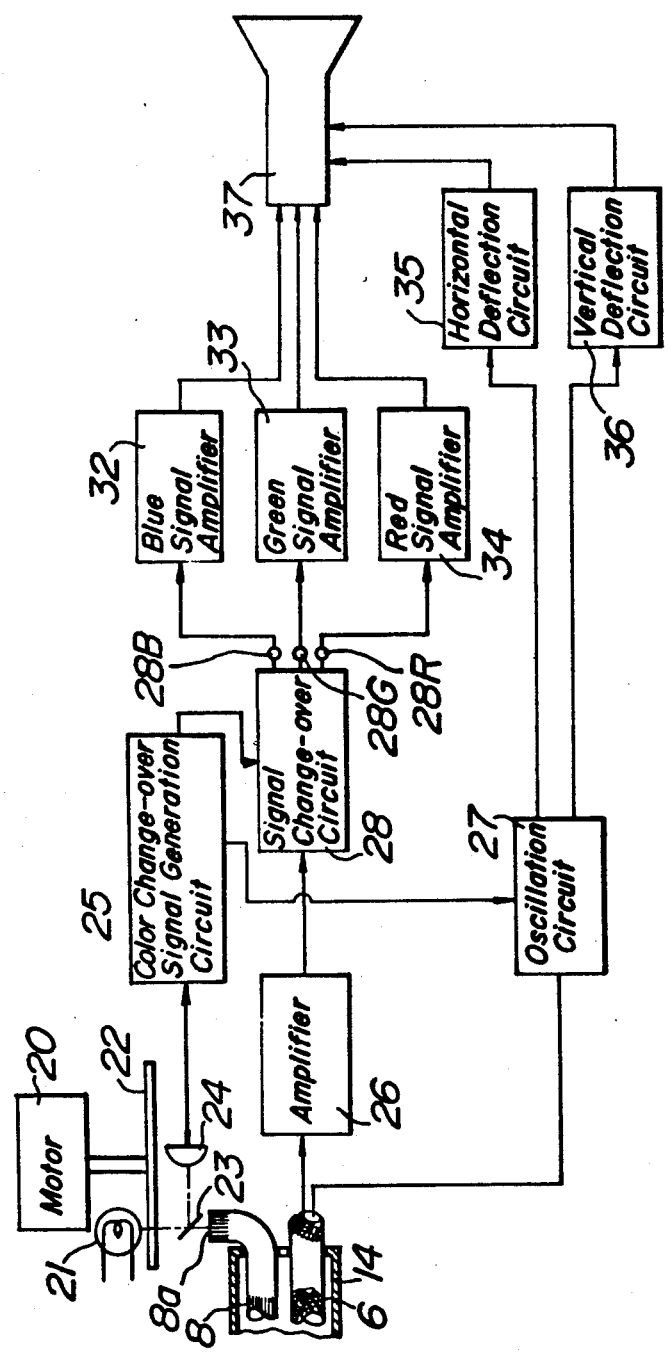
FIG. 2 is a block diagram for illustrating one embodiment of a circuit arranged outside the part shown in FIG. 1 of the endoscope according to the invention.
Figure 6:
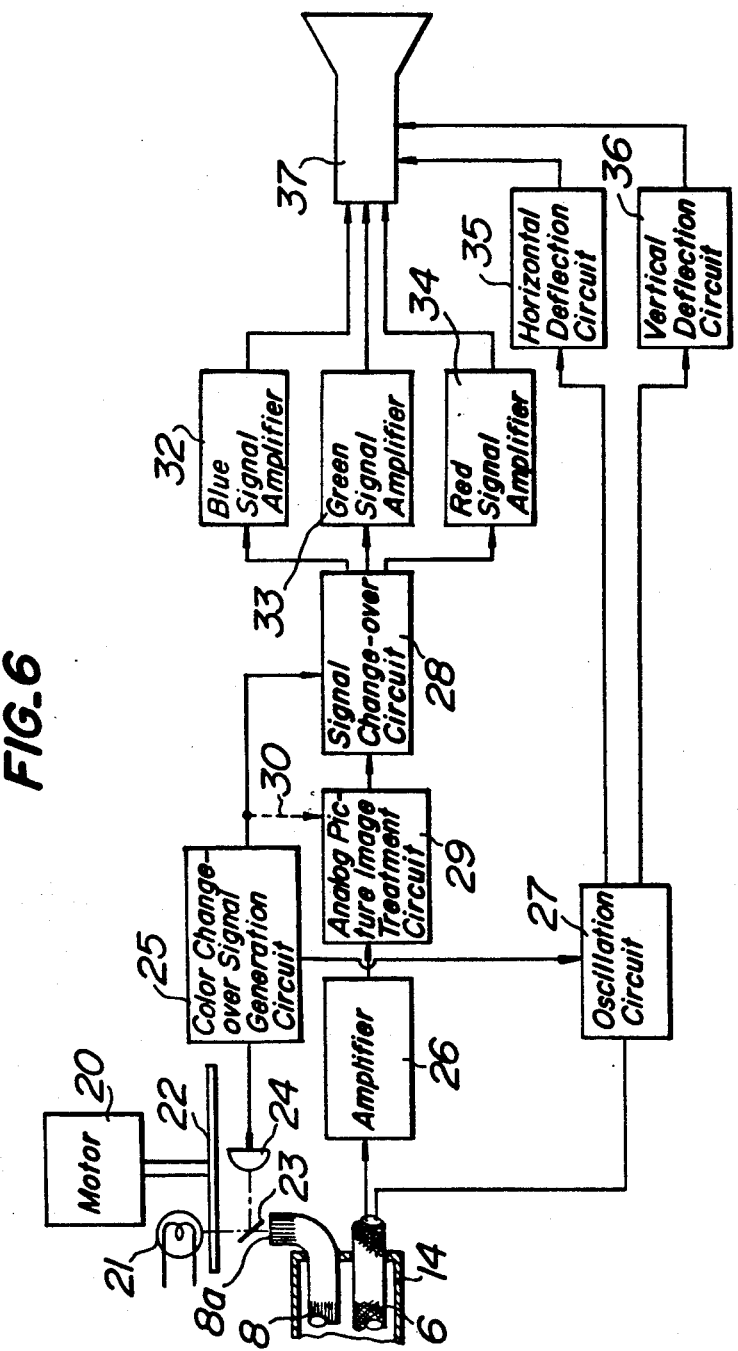
Figure 7:
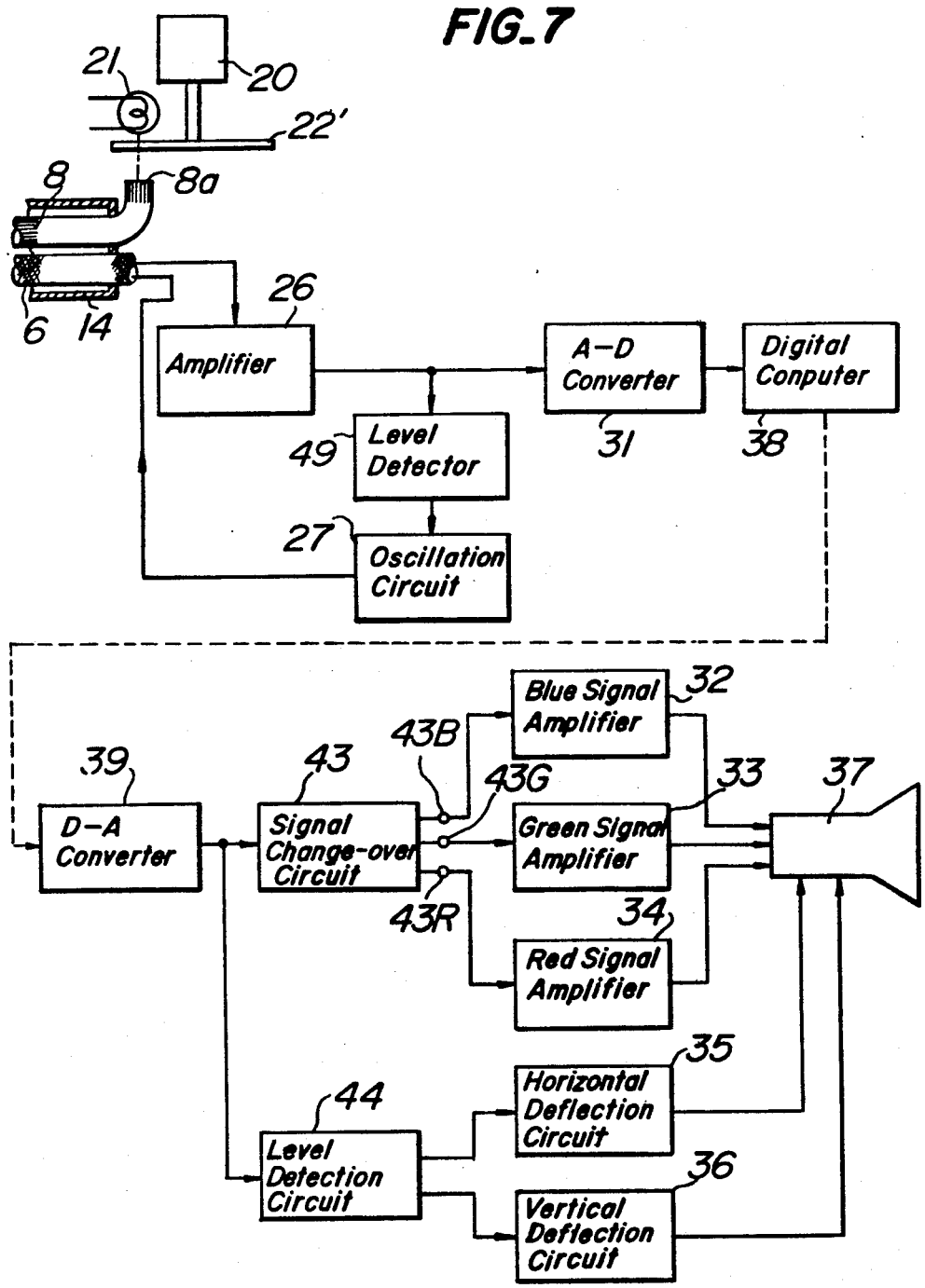
Figure 8:
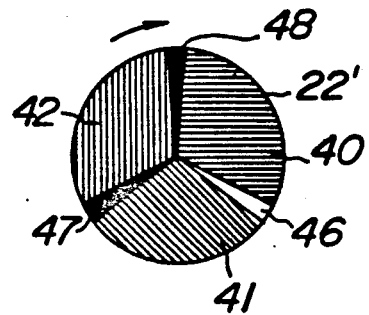
Figure 9:
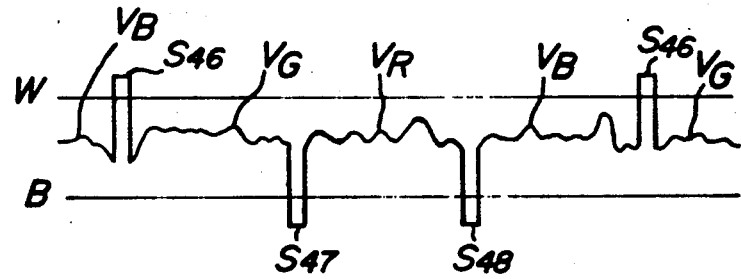
Figure 10:
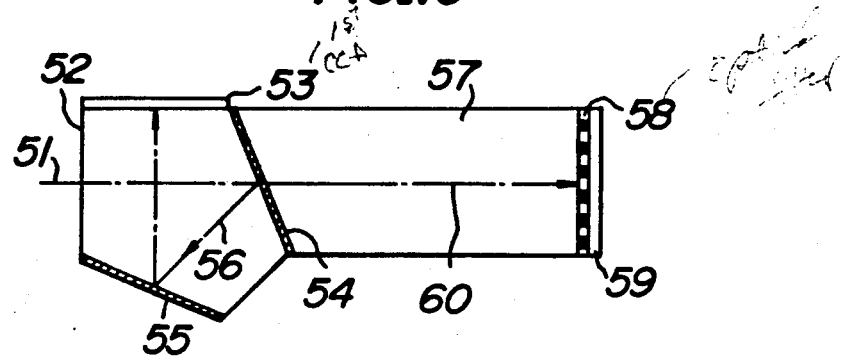
Figure 11:
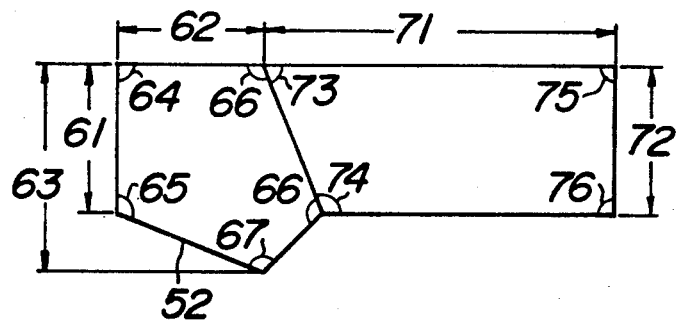
Figure 12:
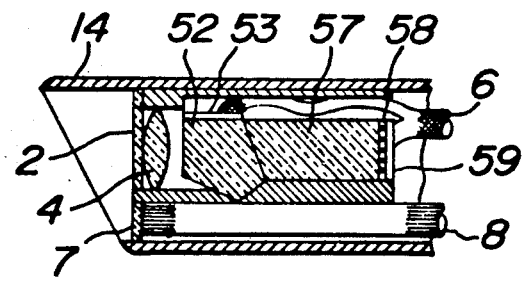
Figure 13:
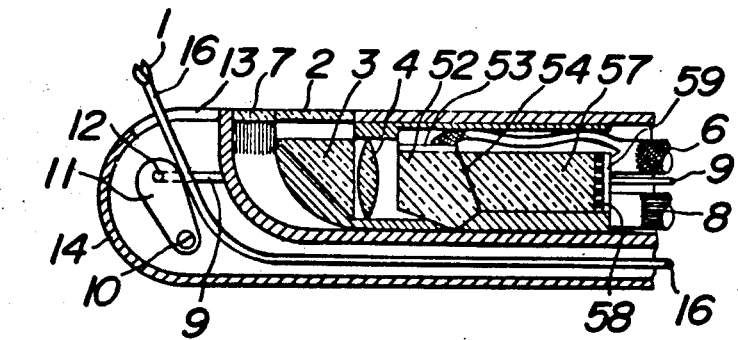
Figure 14:
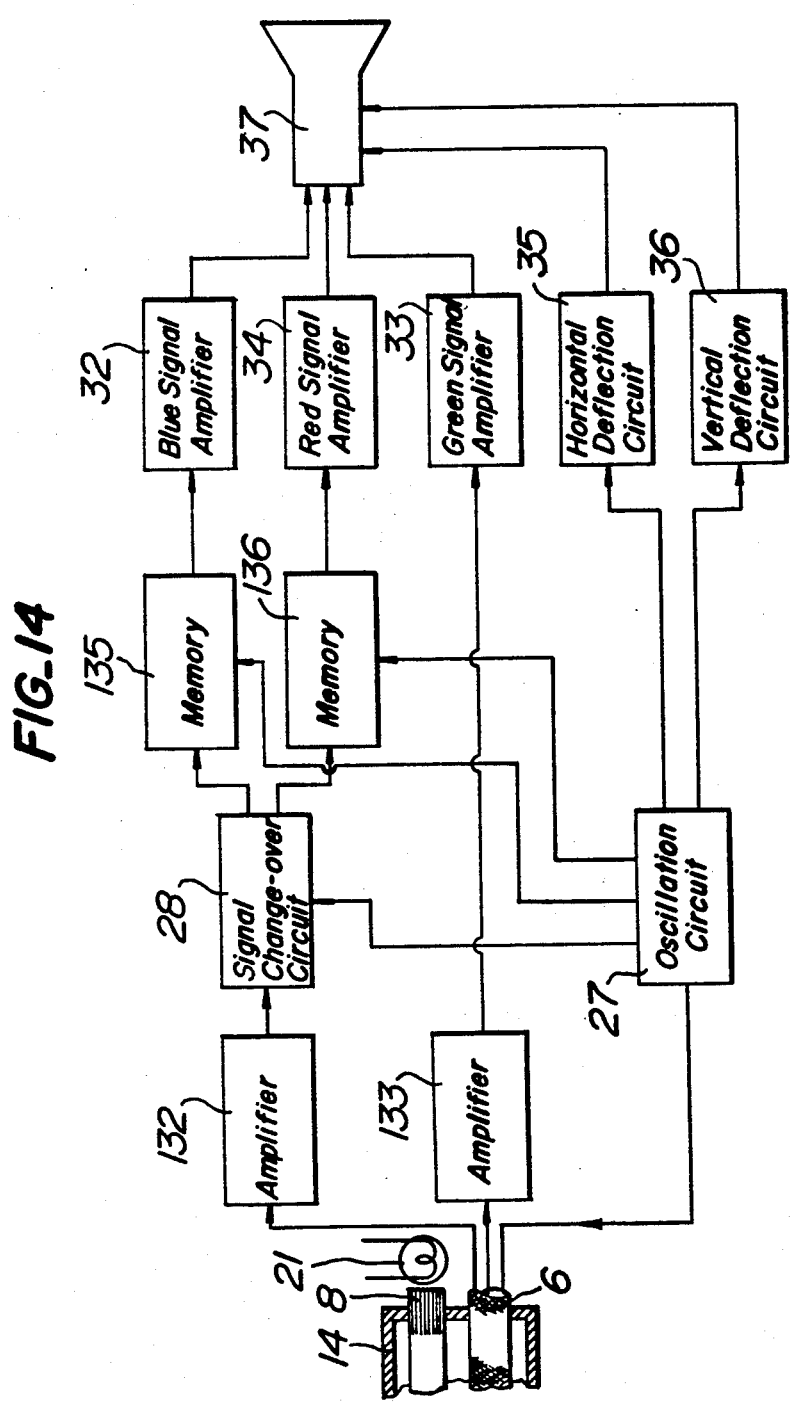
Figure 15:
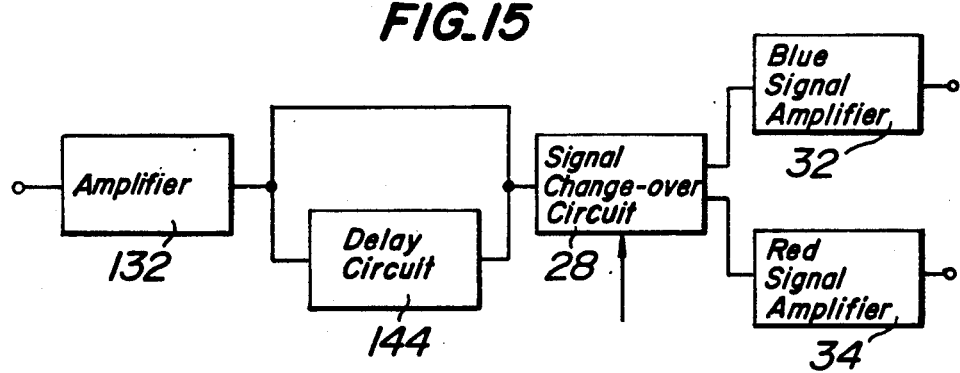
Figure 16:
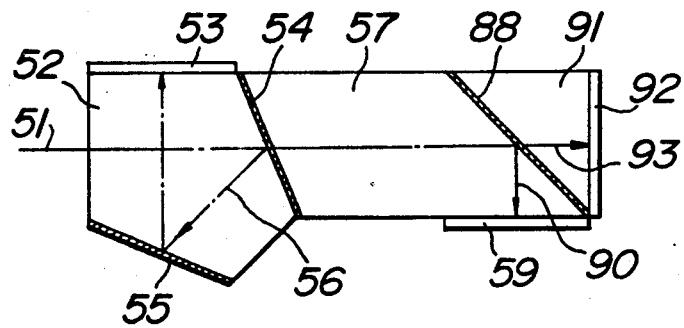
Figure 17:
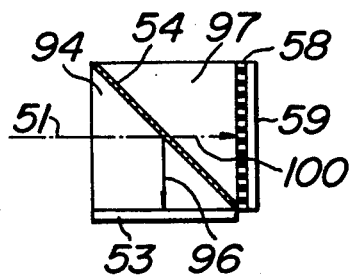
Figure 18:
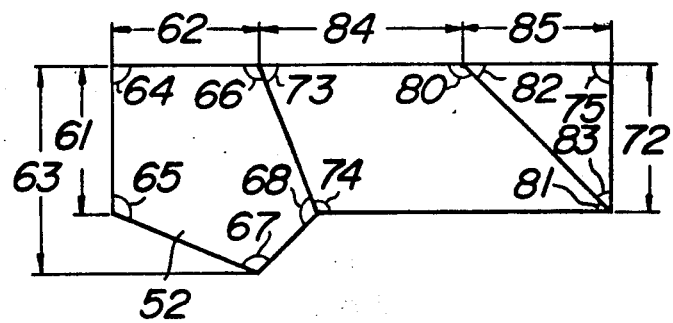
Figure 19:
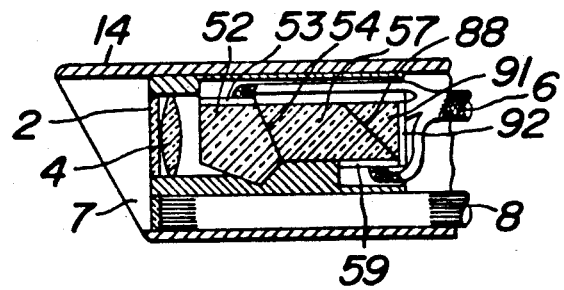
Figure 20:
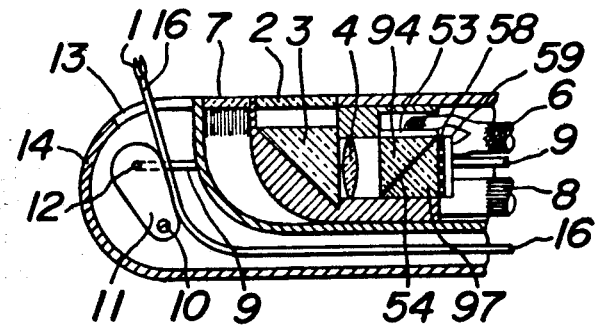
Figure 21:
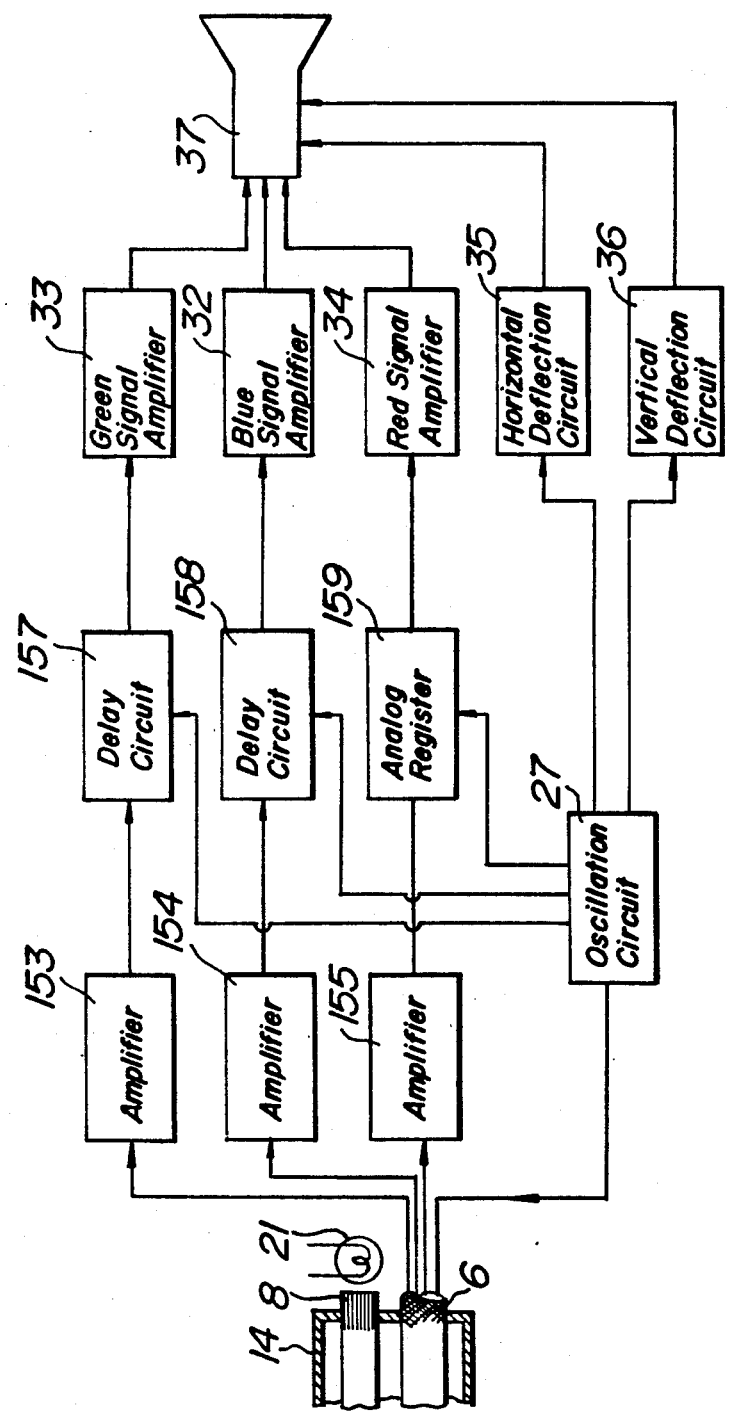
Figure 22:
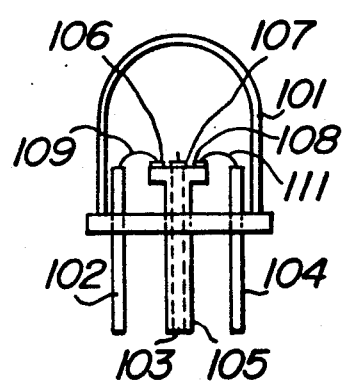
Figure 23:
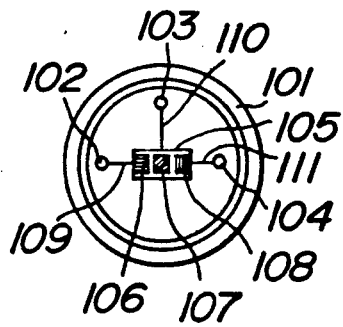
Figure 25:
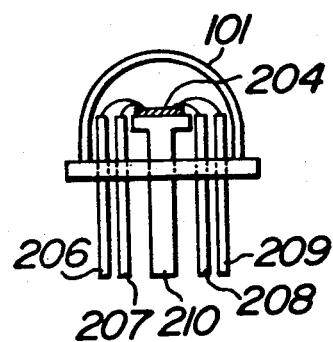
Figure 26:
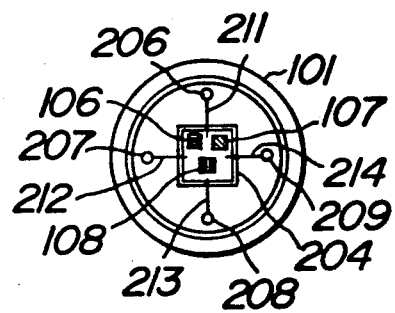
Figure 24:
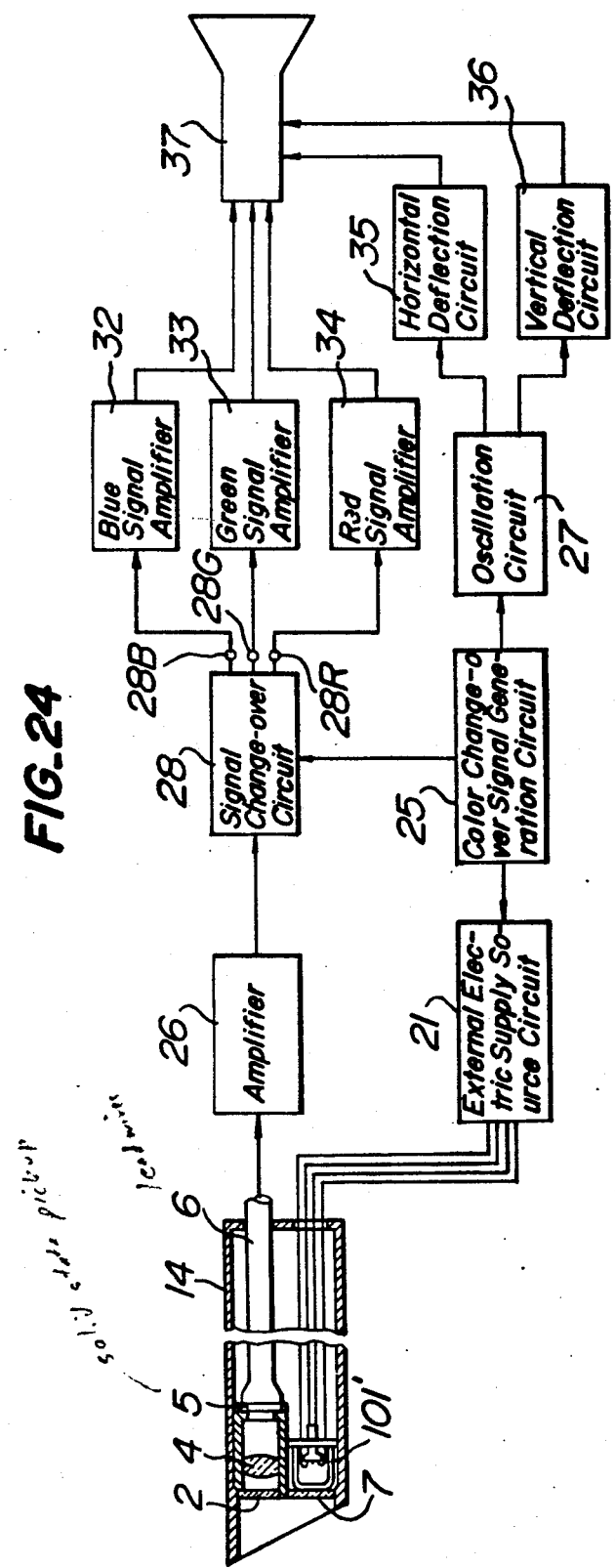
Figure 27:
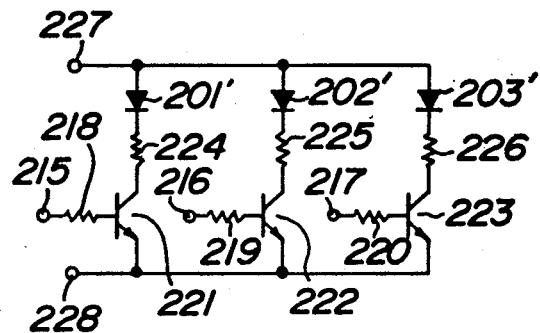
Figure 28:
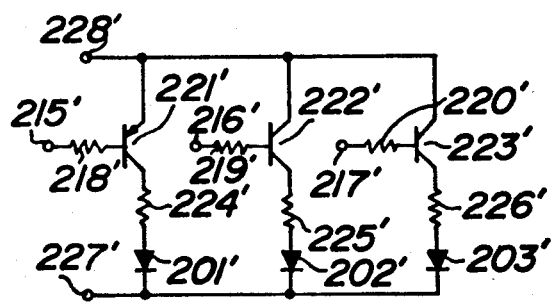
Figure 29:
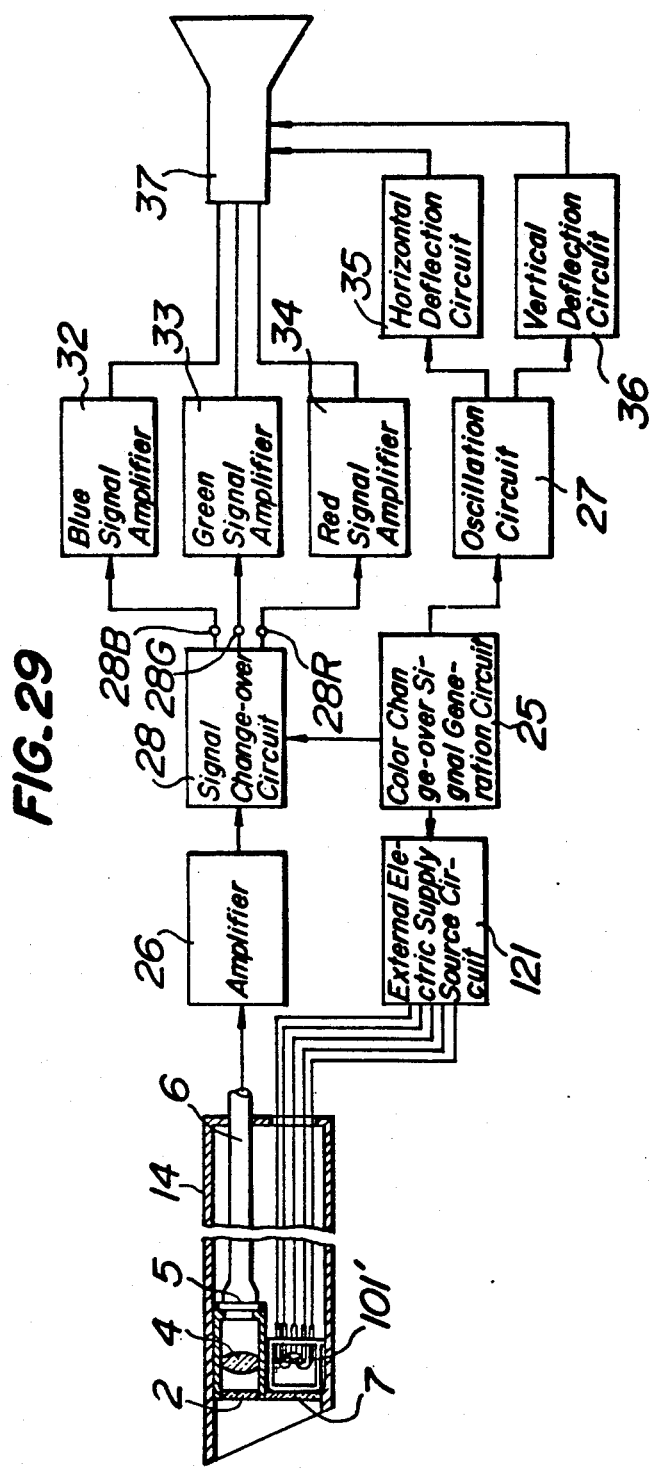
Figure 33:
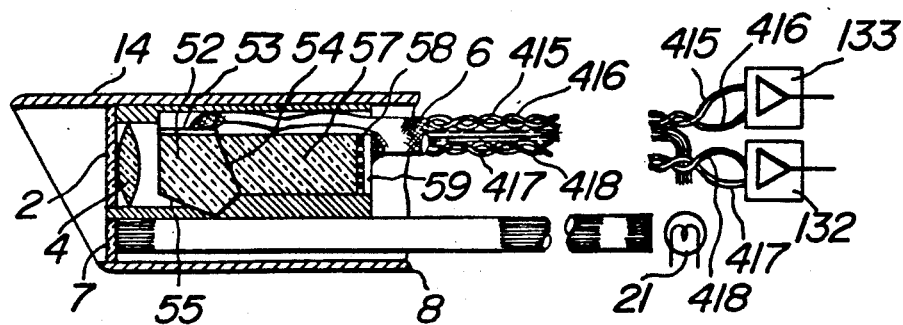
Figure 34A:
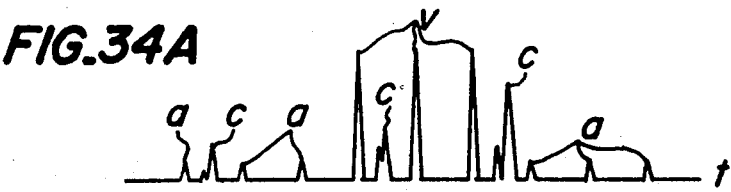
Figure 34B:
Figure 34C:
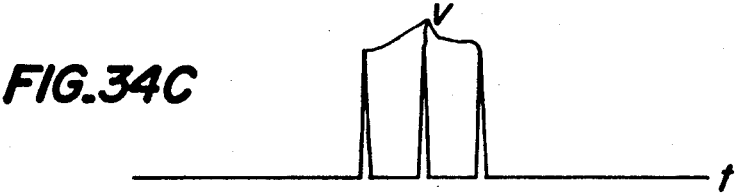

FIGS. 3 and 4 diagrammatically illustrate a relation between a tricolor filter and a light inlet end surface of a light transfer conductor shown in FIG. 2;

FIG. 5 is a partial sectional view showing a modified embodiment of the part shown in FIG. 1;

FIG. 6 is a block diagram for illustrating another embodiment of a circuit arranged outside the parts shown in FIGS. 1 and 5 of the endoscope according to the invention;

FIG. 7 is a block diagram for illustrating a further embodiment of a circuit arranged outside the parts shown in FIGS. 1 and 5 of the endoscope according to the invention;

FIG. 8 is a plan view showing one embodiment of a tricolor filter used for the circuits shown in FIGS. 2, 6 and 7;

FIG. 9 is a graph showing a signal wave for illustrating an operation for detecting color change-over signals;

FIG. 10 is a sectional view showing one embodiment of a light decomposition optical system adapted to be enclosed in the parts shown in FIGS. 1 and 5;

FIG. 11 diagrammatically illustrates the minimum dimensions of the light decomposition optical system shown in FIG. 10;

FIG. 12 is a partial sectional view showing a further embodiment of that part of an endoscope according to the invention which is inserted into a hollow cavity and comprises a light decomposition optical system shown in FIG. 10;

FIG. 13 is a partial sectional view showing a modified embodiment of the part shown in FIG. 12;

FIG. 14 is a block diagram for illustrating one embodiment of a circuit arranged outside the parts shown in FIGS. 12 and 13 of the endoscope according to the invention;

FIG. 15 is a block diagram for illustrating a modified embodiment of the circuit shown in FIG. 14;

FIG. 16 is a sectional view showing another embodiment of a light decomposition optical system adapted to be enclosed in the part shown in FIG. 1;

FIG. 17 is a sectional view showing a further embodiment of a light decomposition optical system adapted to be enclosed in the part shown in FIG. 5;

FIG. 18 diagrammatically illustrates the minimum dimensions of the light decomposition optical system shown in FIG. 16;

FIG. 19 is a partial sectional view showing a still further embodiment of that part of an endoscope according to the invention which is inserted into a hollow cavity and comprises a light decomposition optical system shown in FIG. 16;

FIG. 20 is a partial sectional view showing a modified embodiment of the part shown in FIG. 19, which comprises a light decomposition optical system shown in FIG. 17;

FIG. 21 is a block diagram for illustrating one embodiment of a circuit arranged outside the parts shown in FIGS. 19 and 20 of the endoscope according to the invention;

FIG. 22 is a front elevational view showing one embodiment of a solid state light emitting device according to the invention;

FIG. 23 is its plan view;

FIG. 24 is a block diagram for illustrating one embodiment of an endoscope according to the invention which makes use of the solid state light emitting device shown in FIGS. 22 and 23;

FIG. 25 is a front elevational view showing another embodiment of the solid state light emitting device according to the invention;

FIG. 26 is its plan view;

FIG. 27 is a circuit diagram showing one embodiment of circuit elements enclosed in the package shown in FIGS. 25 and 26;

FIG. 28 is a circuit diagram showing another embodiment of circuit elements enclosed in the package shown in FIGS. 25 and 26;

FIG. 29 is a block diagram for illustrating one embodiment of an endoscope according to the invention which makes use of the solid state light emitting device shown in FIGS. 25 and 26 and the circuit elements shown in FIG. 27 or FIG. 28;

FIG. 30 is a fragmentary perspective view showing the light decomposition optical system shown in FIG. 10 and provided at its side surfaces with contacts connecting wires;

FIG. 31 is a perspective view showing one embodiment of a receptacle detachably engageable with the light decomposition optical system shown in FIG. 30;

FIG. 32 is a block diagram for illustrating the circuit shown in FIG. 14 arranged outside the part shown in FIG. 12 which makes use of the light decomposition optical system shown in FIGS. 30 and 31;

FIG. 33 is a partial sectional view showing that part of the endoscope according to the invention which is inserted into a hollow cavity shown in FIG. 12 and comprises pairs of picture image signal wires and driving compensation signal wires, each pair of picture image signal wire and driving compensation signal wire being twisted together along their overall length; and FIGS. 34A, 34B and 34C are graphs showing signal waves which illustrate operation of the part of the endoscope shown in FIG. 33.

Referring now to FIG. 1 showing one embodiment of that part of the endoscope according to the invention which is inserted into a hollow cavity, the present embodiment of the part shown in FIG. 1 is of a direct view type. A light emitted from a light source 21 (FIG. 2) is transmitted through a light transfer body 8 and a glass window 7 onto an object to be visualized. A light reflected by the object to be visualized is transmitted through a glass window 2 and a lens 4 onto a light receiving surface of a self-scanning type solid state image pick-up device 5 to form an image of the object to be visualized onto the light receiving surface. The solid state image pick-up device 5 is composed of a number of photosensitive elements arranged on a flat plane. The output signal delivered from the solid state image pick-up device 5 is transmitted through a bundle of lead wires 6 to the outside of the part. The bundle of lead wires 6 is inclusive of a lead wire for supplying a clock signal from an oscillation circuit 27 (FIG. 2) to the solid state image pick-up device 5, the clock signal serving to operate the solid state image pick-up device 5. Both the light transfer body 8 and the bundle of lead wires 6 are inserted into a sheath 14. In addition, the lens 4 and the solid state image pick-up device 5 are arranged in a casing 15 enclosed in the sheath 14.

In FIG. 2 is shown one embodiment of a circuit arranged outside the part shown in FIG. 1. To a light inlet end surface 8a of the light transfer body 8 projected from the rear end of the sheath 14 is opposed the light source 21. Between the light source 21 and the end surface 8a are arranged a tricolor filter 22 and a half reflecting mirror 23. The tricolor filter 22 is rotated at a given speed by means of a motor 20.

The tricolor filter 22 is equally divided into three segments 40, 41 and 42 as shown in FIG. 3, the segment 40 transmitting a blue light having a center wave length of 450 nm, the segment 41 transmitting a green light having a center wave length of 540 nm and the segment 42 transmitting a red color having a center wave length of 600 nm. As a result, a liht incident on the light inlet end surface 8a of the light transfer body 8 is changed in succession in the order of blue, green and red light in a given period.

In this case, the light inlet end surface 8a may be made circular in section as shown by dotted lines in FIG. 3 or slit-shape in section as shown by dotted lines 8a' in FIG. 4. When the tricolor filter 22 is rotated at a constant speed, it is desirous to make the light inlet end surface 8a of the light transfer body 8 slit-shape as shown in FIG. 4 by taking the changing over time at the boundary between the two color lights into consideration. But, in the case of manufacturing the end surface 8a of the light transfer body 8, it is easier to make the end surface 8a circular in section as shown in FIG. 3. In the case of making the light inlet surface 8a of the light transfer body 8 circular in section, in order to make the change-over time at each color light short, it is possible to make the diameter of the tricolor filter 22 large and arrange the end surface 8a of the light transfer body 8 at a position near the outer periphery of the tricolor filter 22.

The light reflected by the half reflecting mirror 23 is incident on a light receiving element 24 whose output is supplied to a color change-over signal generation circuit 25. If the light receiving element 24 is composed of a phototransistor or a photdiode, a ratio among the levels of output from the tricolor filter 22 with respect to the blue, green and red lights becomes 1:4:6. The color change-over signal generation circuit 25 consists of a current amplifier and a level detection circuit and serves to convert the output current signal from the light receiving element 24 into a voltage signal and form timing signals of the blue, green and red lights, respectively, by means of the level detection circuit. In addition, the output from the current amplifier of the color change-over signal generation circuit 25 is differentiated so as to align the level thereof to form a trigger signal which is then supplied to an oscillation circuit 27. A picture image signal delivered from the solid state image pick-up device 5 through the bundle of lead wires 6 to the outside of the sheath 14 is supplied through an amplifier 25 to a signal change-over circuit 28 which is then operated to supply the picture image signal to respective output terminals 28B, 28G and 28R in synchronism with the kinds of color of the light incident on the light transfer body 8.

The signal change-over circuit 28 makes use of a high speed operation switch such as a semiconductor analog switch, etc. The oscillation circuit 27 receives the trigger signal from the color change-over signal generation circuit 25 and supplies a scanning signal to the image pick-up device 5 and synchronizing signals to a horizontal deflection circuit 35 and a vertical deflection circuit 36, respectively. The horizontal deflection circuit 35 is composed of an output amplifier for sweeping each of blue, green and red lights in the horizontal direction and the vertical deflection circuit 36 is composed of an output amplifier for sweeping each of blue, green and red lights in the vertical direction.

The outputs from the output terminals 28B, 28G and 28R of the signal change-over circuit 28 are supplied to blue, green and red amplifiers 32, 33, 34, respectively, which amplify the outputs from the output terminals 28B, 28G and 28R to voltages which are sufficient to operate blue, green and red grids of a Braun tube 37.

In the case of displaying a color picture image with the aid of, for example, a field sequential system, the tricolor filter 22 is rotated such that the blue, green and red light portions of the tricolor filter 22 are changed over with a field period. The color change-over signal generation circuit 25 serves to generate a color change-over signal synchronized with the rotation of the tricolor filter 22. As a result, during a field period in which the blue light is incident on the light transfer body 8, the output from the amplifier 26 appears at the blue light output terminal 28B and then is supplied through the blue light amplifier 32 to the blue light grid of the Braun tube 37, thereby displaying a blue light image on a screen of the Braun tube 37. Similarly, during the next field period, a green light image is displayed on the screen of the Braun tube 37 and during the next field period, a red light image is displayed on the screen of the Braun tube 37. As a result, the blue, green and red light images which are changed over every successive periods are visually composed to from a color picture image to be visualized.

In FIG. 5 is shown another embodiment of that part of the endoscope according to the invention which is inserted into the hollow cavity. In the present embodiment, the same reference numerals as those shown in FIG. 1 designate the same parts as those shown in FIG. 1. The present embodiment is of a side view type. The light outlet end of the light transfer body 8 is bent sidewardly and the sheath 14 is provided at its one side with the glass window 7 which is opposed to the light outlet end of the light transfer body 8. The light reflected from the object to be visualized is taken through the glass window 2 provided on the side surface of the sheath 14 thereinto. A prism 3 causes the light to change its direction and the light is then incident on the light receiving surface of the self-scanning type solid state image pick-up device 5 by means of the lens 4. In the present embodiment, a forceps 1 is projected through a glass window 13. The forceps 1 is used to pick-up a living body structure. The front end of a wire 9 extending through the sheath 14 is secured to a hole 12 formed at one end of a lever 11 pivotally mounted at its another end on a screw 10. If the wire 9 is pulled out, the lever 11 becomes rotated to change its inclined angle. Thus, the operation of the wire 9 permits the forceps 1 to locate at any desired position of the living body structure. In addition, the forceps 1 is secured to the front end of a cable 16 extending through the sheath 14. Thus, it is possible to pick-up the living body structure by operating the cable 16. As a result, the sheath 14 encloses therein the bundle of lead wires 6, light transfer body 8, cable 16 for driving the forceps 1 and wire 9 for controlling the position of the forceps 1.

In FIG. 6 is shown a block diagram illustrating a modified embodiment of the circuit shown in FIG. 2 which is arranged at the outside of the hollow cavity. In the present embodiment, between the amplifier 26 and the signal change-over circuit 28 is inserted an analog picture image treating circuit 29. In the analog picture image treating circuit 29, the picture signal is differentiated to mkae its contour conspicuous and is subjected to filtering treatment by a band pass filter or a low pass filter to form an easily discernible picture image. In this case, if each of the blue, green and red light picture image signals is subjected to the different treatment, the timing signal from the color change-over generation circuit 25 may be supplied through a conductor 30 to the analog picture image treating circuit 29.

In FIG. 7 is shown a block diagram illustrating another modified embodiment of the circuit shown in FIG. 2 which is arranged at the outside of the hollow cavity. In the present embodiment, the same reference numerals as those shown in FIGS. 2 and 6 designate the same parts as those shown in FIGS. 2 and 6. In the present embodiment, the picture image is digitally treated by means of a digital computer. In addition, instead of taking out a part of the illumination light so as to form the color change-over timing signal, use is made of a tricolor filter 22' shown in FIG. 8 to form a timing signal. The tricolor filter 22' is provided at a boundary between the blue light transmitting portion 40 and the green light transmitting portion 41 with a transparent portion 46 having a given width, provided at a boundary between the green light transmitting portion 41 and the red color transmitting portion 42 with an opaque portion 47 having a given width, and provided at a boundary between the red light transmitting portion 42 and the blue light transmitting portion 40 with an opaque portion 48 having a given width.

The tricolor filter 22' is inserted between the light source 21 and the light inlet end surface 8a of the light transfer body 8 and rotated at a given number of rotations by means of the motor 20. In this case, the picture image signal supplied from the self-scanning type solid state image pick-up device 5 through the bundle of lead wires 6 to the outside may be shown, for example, in FIG. 9. In FIG. 9, $V_B$, $V_G$ and $V_R$ designate blue, green and red picture image signals, respectively, and S46, S47 and S48 are color synchronizing signals generated by the transparent portion 46, and opaque portions 47 and 48, respectively. The signal S46 is higher than a white level W and the signals S47 and S48 are lower than a black level B. So, the output signal from the amplifier 26 is supplied to a level detector 49 which can detect the color synchronizing signals S46, S47 and S48 on the basis of their levels so as to form blue, green and red light synchronizing signals which are supplied as trigger signals to the oscillation circuit 27.

In addition, the output picture image signals from the amplifier 26 is supplied to an A-D converter 31 to convert an analog signal into a digital signal which is then supplied to a digital computer 38. In the digital computer 38, the picture image is digitally treated and recognition of pattern, $\gamma$ control, superimposition of the treated picture images, etc. are digitally effected.

In this case, if an instantaneous treatment is required, the A-D converter 31 must be rapid in conversion speed and small in number of bits. For example, the conversion speed must be 100 $\mu$s to 1 $\mu$s and the number of bits must be on the order of 4 to 5 bits. If the instantaneous treatment is not required, the conversion speed of the A-D converter 31 may be made slow by making the number of rotations of the motor 20 small and by making the amount of light of the light source 21 or the gain of the amplifier 26 small.

The digital picture image signal treated by the digital computer 38 is supplied to a D-A converter 39 and converted into an analog signal which is supplied to a signal change-over circuit 43 and a level detection circuit 44. The signal change-over circuit 43 serves to effect level detection so as to detect the above mentioned color synchronizing signals and supplies blue, green and red light signals to blue, green, red light output terminals 43B, 43G, 43R, respectively. The level detection circuit 44 detects the color synchronizing signals which are supplied as trigger signals to the horizontal deflection circuit 35 and vertical deflection circuit 36.

In FIG. 10 is shown one embodiment of a light decomposition optical system used for the endoscope according to the invention. In the present embodiment, a light 51 reflected by an object to be visualized and passed through the lens 4 (FIG. 12) is incident on a pentaprism 52 and a green light 56, for example, is reflected by a dichroic mirror 54 and blue and red lights are transmitted therethrough and pass straight ahead. The green light 56 reflected by the dichroic mirror 54 is reflected again by a reflecting mirror 55 and incidents on a first solid state image pick-up device 53. The light 60 transmitted through the dichroic mirror 54 passes through a light transmission block 57 and arrives at an optical filter such as a stripe filter 58 which can decompose the light 60 into the blue and red lights. The blue and red lights are incident on a second solid state image pick-up device 59.

In FIG. 11 is shown the minimum dimensions of the light decomposition optical system shown in FIG. 10. In the endoscope, that part thereof which is inserted into the hollow cavity must be made as small as possible. The light decomposition optical system enclosed in the front end part of the endoscope occupies the largest space if compared with the space occupied by any other constitutional elements enclosed in the front end part of the endoscope, and as a result, the dimension of the light decomposition optical system must be made minimum. Particularly, it is important to make a length 63 of the pentaprism 52 small. Calculations have yielded the following lengths and angles.

Let lengths 61, 62, 72 be $a$, the length 63 is given by $a(\tan(\pi/8) + 1)$ and a length 71 is given by $a(1 + \sqrt{2})$. Angles 64, 75 and 76 are $\pi/2$ radians, angles 65, 66, 67, 74 are $\frac{5}{8}\pi$ radians, respectively, and an angle 73 is $\frac{3}{8}\pi$ radians.

In FIG. 12 is shown one embodiment of that part of the endoscope according to the invention which is inserted into the hollow cavity and which comprises the light decomposition optical system shown in FIG. 10. The part shown in FIG. 12 is of a direct view type.

In the present embodiment, a light from the light source is passed through the light transfer body 8 and the glass window 7 and illuminates an object to be visualized.

A light reflected by the object to be visualized is taken through the glass window 2 into the sheath 14. The image of the object to be visualized is formed by the lens 4, pentaprism 52, light transmission block 7, solid state image pick-up devices 53, 59 and decomposed and changed into electric signals. The bundle of lead wires 6 encloses therein a lead wire through which is passed a signal for driving the solid state image pick-up devices 5, 9 and a lead wire for deriving image signals from the solid state image pick-up devices 53, 59.

In FIG. 13 is shown another embodiment of the side view type of that part of the endoscope according to the invention, which comprises the light decomposition optical system shown in FIG. 10. In the present embodiment, a light from the light source is led through the light transfer body 8 into the sheath 14 and illuminate an object to be visualized through the glass window 7. A light reflected by the object to be visualized is taken through the glass window 2 into the sheath 14 and an image of the object to be visualized is formed by the prism 3, lens 4, pentaprism 52, light transmission block 57 and solid state image pick-up devices 53, 59, and decomposed and changed into electric signals. The other construction and the operation thereof are substantially the same as those described with reference to FIG. 5.

FIG. 14 is shown another embodiment of a circuit arranged outside the part shown in FIG. 12 or FIG. 13. In the present embodiment, use is made of a lamp as the light source 21 and a light from the light source 21 is led through the light transfer body 8 into the hollow cavity. The oscillation circuit 27 supplies a signal for driving the solid state image pick-up devices 53, 59, signals for driving memories 135, 136 which can memorize the image signal, and synchronizing signals used for the horizontal deflecting circuit 35 and vertical deflecting circuit 36 for sweeping electron beams of the color Braun tube 37. In the present embodiment, the dichroic mirror 54 serves to reflect the green light and transmit the red and blue lights therethrough and the optical filter 58 is composed of a stripe filter for decomposing the red light and the blue light alternately every one horizontal scanning period. The output signal from the first image pick-up device 53, that is, the green light image signal is amplified by an amplifier 133 and then amplified by the green amplifier 33 to a voltage which is sufficient to operate a green grid of the color Braun tube 37. The image signal from the second solid state image pick-up device 59 is amplified by an amplifier 132 and supplied to the signal change-over circuit 28 which can change-over the image signal into red and blue light signals by the synchronizing signal received from the oscillation circuit 27. The blue and red light signals are memorized in memories 135 and 136 and then supplied to the blue and red light amplifiers 32, 34, respectively. During one horizontal scanning period, one of the color signals is memorized in the memory and during the next one horizontal scanning period, the other color signal is memorized in the memory.

At the same time, the color signals previously memorized are supplied to the blue and red light amplifiers 32, 34, respectively. In the present embodiment, the signal change-over circuit 28 makes use of a high speed operation switch such as a semiconductor analog switch, etc.

The endoscope according to the present embodiment is capable of decomposing the impage of the object to be visualized into three color lights to generate respective color signals in that part of the endoscope which is inserted into the hollow cavity, of leading the color signals to the outside and of displaying the color picture image on the color Braun tube. This permits a highly compact construction which is easy in operation if compared with the prior art endoscope which makes use of the vidicon tube.

In the present embodiment, the optical filter 58 is arranged in front of the second solid state image pick-up device 59. Alternatively, the optical filter 58 may be arranged in front of the first solid state image pick-up devices 53. In this case, it is a matter of course that the dichroic mirror 54 must reflect two color lights.

In FIG. 15 is shown a modified embodiment of the circuit shown in FIG. 14. In the present embodiment, the output from the amplifier 132 is supplied directly to and through a delay circuit 144 to the signal change-over circuit 28 whose output is directly supplied to he blue and red light amplifiers 32, 34. In the present embodiment, it is possible to omit the memories 135, the shown in FIG. 14.

In FIG. 16 is shown a modified embodiment of the light decomposition optical system shown in FIG. 10. In the present embodiment, a light 51 reflected by an object to be visualized and passed through the lens 4 (FIG. 19) is incident on the pentaprism 54 which can reflect, for example, a green light 56 and causes blue and red lights to pass straight ahead. The green light 56 reflected by the dichroic mirror 54 is reflected again by the reflecting mirror 55 and incident on the first solid state imge pick-up device 53. The light transmitted through the dichroic mirror 54 passes through the light transmission block 57. A red light 90, for example, is reflected by a dichroic mirror 88 and a blue light 93 transmits therethrough and passes straight ahead. The red light 90 reflected by the dichroic mirror 88 is incident on the second solid state image pick-up device 59 and the blue light 93 transmitted through the dichroic mirror 88 is transmitted through a light transmission block 91 and incident on a third solid state image pick-up device 92.

In FIG. 17 is shown another embodiment of a light decomposition optical system used for the endoscope according to the invention. In the present embodiment, the light 51 reflected by an object to be visualized and passed through the prism 3 and the lens 4 (FIG. 20) is incident on a light transmission block 94 and a green light 96, for example, is reflected by the dichroic mirror 54 and the blue and red lights 100 are transmitted through the dichroic mirror 54 and pass straight ahead.

The green light 96 reflected by the dichroic mirror 54 is incident on the first solid state image pick-up device 53 and the light 100 transmitted through the dichroic mirror 54 pass through a light transmission block 97 and arrive at the optical filter 58 such as the stripe filter which can decompose the lights into blue and red lights which incident on the second solid state image pick-up device 59.

In FIG. 18 is shown the minimum dimensions of the light decomposition optical system shown in FIG. 16. Calculations have yielded the following lengths and angles. Let lengths 61, 62, 72, 85 be $a$, the length 63 is also given by a $(\tan(\pi/8) + 1)$ similar to the embodiment shown in FIG. 10 and a length 84 is given by $a\sqrt{2}$. Angles 64 and 75 are $\pi/2$ radians, angles 65, 66, 67, 68 and 74 are $\frac{3}{8}\pi$ radians, an angle 80 is $\frac{3}{4}\pi$ radians, an angle 73 is $\frac{3}{8}\pi$ radians and angles 81, 82 and 83 are $\pi 4$ radians, respectively.

In FIG. 19 is shown one embodiment of that part of the endoscope according to the invention which is inserted into the hollow cavity and which comprises the light decomposition optical system shown in FIG. 16. The part shown in FIG. 19 is of a direct view type. In the present embodiment, a light from the light source is led through the light transfer body 8 into the sheath 14 and illuminated through the glass window 7 on an object to be visualized. A light reflected by the object to be visualized is taken through the glass window 2 into the sheath 14 and the image of the object to be visualized is formed, decomposed and changed into electric signals by the lens 4, pentaprism 52, light transmission blocks 57, 91 and image pick-up devices 53, 59, 92. Similar to the embodiment shown in FIG. 12, the bundle of lead wires 6 encloses therein lead wires for deriving the image signals from the image pick-up devices 53, 59 and 92.

In FIG. 20 is shown a further embodiment of the side view type of that part of the endoscope according to the invention, which comprises the light decomposition optical system shown in FIG. 17.

In the present embodiment, the light from the light source (FIG. 21) is lead through the light transfer body 8 into the sheath 14 and illuminates through the glass window 7 the object to be visualized. The light reflected by the object to be visualized is taken through the glass window 2 into the sheath 14 and the image of an object to be visualized is formed, decomposed and changed into electric signals by the prism 3, lens 4, light transmission blocks 94, 97, stripe filter 58 and image pick-up devices 53, 59. The other construction and the operation thereof are substantially the same as those described with reference to FIG. 5.

In FIG. 21 is shown a further embodiment of the circuit arranged outside the sheath 14 shown in FIG. 19. In the present embodiment, a lamp is used as the light source 21 for illuminating an object to be visualized. The light from the light source 21 is led through the light transfer body 8 into the hollow cavity. The oscillation circuit 27 supplies signals for driving the image pick-up devices 53, 55, 92 and synchronizing signals to an analog register 159 for reversing the image signal during one horizontal period and to the horizontal deflection circuit 35 and vertical deflection circuit 36 for sweeping the electron beams in the color Braun tube 37. In the present embodiment, the dichroic mirror 54 reflects the green light and transmits the red and blue lights and the dichroic mirror 88 reflects the red light and transmits the blue light. The green light 56 is reflected again by the reflecting mirror 55 and incident on the solid state image pick-up device 53, so that the green light is reflected twice times in total. The red light 90 is reflected by the dichroic mirror 88 one time only. The blue light 93 is transmitted through both the dichroic mirrors 54, 88 and hence is not reflected at all.

As a result, the red light is reversed with respect to the green and blue lights and hence it is necessary to reverse the output electric signal for the red light with respect to the output electric signals for the other color lights within one scaning period. For this purpose, the green image signal from the image pick-up device 53 is amplified by an amplifier 253 and supplied to a delay circuit 157 for delaying the signal by one horizontal scanning period and then amplified by the green amplifier 33 to a voltage which is sufficient to operate the green grid of the color Braun tube 37. The blue image signal from the image pick-up device 92 is amplified by an amplifier 154 and supplied to a delay circuit 158 for delaying the signal by one horizontal scanning period and then amplified by the blue light amplifier 32 to a voltage which is sufficient to operate the blue light grid of the color Braun tube 37. The red image signal from the image pick-up device 59 is amplified by an amplifier 155 and supplied to an analog register 159 for reversing the red image signal within one horizontal scanning period and then amplified by the red amplifier 34 to a voltage which is sufficient to operate the red light grid of the color Braun tube 37. By reversing the red image signal within one horizontal scanning period, it is possible to correct the difference between the number of reflections of the signals and hence display a correct color picture image. The difference between the number of reflections of the signals can be corrected by inserting extra reflecting surfaces into the light decomposition optical system. In this case, however, the light decomposition optical system to be enclosed in the front end part of the endoscope becomes large in size and hence such measure is not suitable in practice.

In the case of reversing the image signal during one horizontal scanning period, use may be made of an analog image signal or a digital image signal converted from the analog image signal. In the case of using the analog image signal, in the first place, a combination of a condenser and a switch may be used and secondly, use may be made of a semiconductor electric charge transfer element. In the first case, condensers whose number corresponds to the number of picture elements of one line of the image signal and a switch for selecting one of these condensers are used. These condensers are charged with an amount of electric charge which is proportional to the brightness of the picture elements in a given order and outputs are derived in the order which is reversal to the charging order, thereby reversing one line of the image signal. In the case of using the digital image signal, accumulation of the electric charge is effected in the same manner as in the case of using the analog image signal. In this case, however, high speed A-D converters are arranged at the succeeding stage of the amplifiers 153, 154, 155 and use is made of a shift register or a random access memory whose output is changed into an analog signal by a D-A converter. In such shift register or memory, elements are connected in series and the input electric charge is transferred by the potential gradient due to the clock signal. An electric charge transfer element having elements whose number is two times larger than the number corresponding to the picture elements of one line of the image signal is used and an electric charge which is proportional to the picture element is injected from the input end in response to the image clock signal. The input electric charge is transferred in succession and accumulated. When accumulation for one line of the image signal has been completed, the potential gradient is reversed and the electric charge is delivered from the input end, thereby reversing one line of the image signal. The digital image signal may be used in the same manner as the analog image signal by additionally effecting A-D conversion and D-A conversion.

In FIGS. 22 and 23 is shown one embodiment of a solid state light emitting device used as a light source. In the present embodiment, in a package 101 at least light emitting portion is transparent are hermetically arranged light emitting chips 106, 107, 108 emitting in blue, green and red, respectively. The package 101 is kept in vacuum or contains a suitable inert gas. A common lead wire 105 led into the package 101 is connected to one of electrodes of the light emitting, chips 106, 107, 108, respectively, and the other electrodes of the light emitting chips 106, 107, 108 are connected through conductors 109, 110, 111 having a high electric conductivity and formed of, for example, gold to lead wires 102, 103, 104, respectively, and led out of the package 101.

The lead wires 102, 103, 104, 105 are connected through conductors to an external electric supply source circuit 121 (FIG. 24) which comprises a switching circuit. The external electric supply source circuit 121 alternately delivers operating signals across the common lead wire 5 on the one hand and the other lead wires 102, 103, 104 on the other hand in succession. As a result, the light emitting chips 106, 107, 108 emit respective color lights in response to the operating signals.

As described above, one package enclosing a plurality of solid state light emitting chips therein provides a highly compact solid state light emitting device which is easy in handling and which can be mounted in the sheath 14 of the endoscope according to the invention in a simple manner.

In FIG. 24 is shown a block diagram illustrating one embodiment of the endoscope according to the invention which comprises the above mentioned solid state light emitting device shown in FIGS. 22 and 23. In the present embodiment, a solid state light emitting device 101' comprising the package 101 at least light outlet portion of which is transparent and the light emitting chips for emitting blue, green and red lights and enclosed in the package 101 and the self-scanning type solid state image pick-up device 5 are provided in the front end portion of the sheath 14 to be inserted into the hollow cavity. The solid state light emitting device 101' is supplied with an operating signal from the external electric supply source circuit 121 and serves to emit light from the light emitting chips in sucession in response to the operating signal. The light thus emitted illuminates through the window 7 an object to be visualized. The light reflected by the object to be visualized is led through the window 2 into the sheath 14 and the image of the object to be visualized is formed on the light receiving surface of the self-scanning type solid state image pick-up device 5. The solid state image pick-up device 5 is composed of a number of photosensitive elements arranged on a flat plane. The output signal from the solid state image pick-up device 5 is led through the bundle of lead wires 6 out of the sheath 14 and amplified by the amplifier 26. The picture image signal from the amplifier 26 is supplied to the signal change-over circuit 28 which supplies the color signals to respective output terminals 28B. 28G, 28R in synchronism with the kinds of color light emitted from the solid state light emitting device 101'. The signal change-over circuit 28 makes use of a high speed operating switch such as a semiconductor analog switch, etc.

The color change-over signal generation circuit 25 comprises a circuit for supplying synchronized clock pulses to the electric supply source circut 121 which makes use of the high speed operating switch sich as the semiconductor analog switch, etc. used for the signal change-over circuit 28 and to the signal change-over circuit 28 and a circuit for supplying trigger pulses to the oscillation circuit 27. The other construction and operation thereof are substantially the same as those described with reference to FIG. 2.

In the case of displaying the color picture image, respective light emitting chips of the solid state light emitting device 1' emit light in response to the clock pulses supplied to the electric supply source circuit 121 including the switching circuit therein from the color change-over signal generation circuit 25. Signals in synchronism with the clock pulses are supplied to the signal change-over circuit 28, and as a result, color signals corresponding to respective emitted light colors appear on the output terminals 28B, 28G, 28R and are supplied through respective color amplifiers 32, 33, 34 to respective grids of the color Braun tube 37. As a result, the blue, green and red images changed over every period of the clock signals are visually composed to form a color picture image to be visualized.

In the embodiments shown in FIGS. 2, 6, 7 which make use of the exterior light source and rotary tricolor filter in order to obtain the image of an object to be visualized, the signal for operating the self-scanning type solid state image pick-up device adapted to form the image of the object to be visualized is synchronized with the rotation of the tricolor filter arranged between the external light source and the light transfer body used for illumination so as to derive the picked-up signals having respective colors. On the contrary, in the embodiment shown in FIG. 24, both the external light source and the tricolor filter are not used and the successive operations of the solid state light emitting chips connected through the conductors to the external electric supply source 121 are synchronized with the picture image signal from the object to be visualized at the signal change-over circuit 28, thereby easily deriving the picked-up signals.

That is, the use of the solid state light emitting device shown in FIGS. 22 and 23 ensures a further simplification of the endoscope and provides the important advantage that the solid state light emitting device can emit light in a stable manner even when it is applied with a low electric voltage so that wires having small diameters can be used as conductors for connecting the external electric supply source to respective lead wires of the solid state light emitting device, and that the solid state light emitting device per se can be made small in size, so that the sectional area of that part of the endoscope which is inserted into the hollow cavity can be made considerably smaller.

The solid state light emitting device shown in FIGS. 22 and 23 is provided in the package with three light emitting chips which emit blue, green and red lights, respectively. Alternatively, provision may be made of at least two light emitting chips for each color light. In this case, the number of the light emitting chips for each color light may be different from each other. In addition, a solid state light emitting device composed of one light emitting chip for emitting three kinds of colors may be provided on one semiconductor substrate. If a reflecting mirror is used in the package, it is possible to emit light sidewardly. Such light emitting device is suitable for use in the side view type endoscope. The package may be formed of a transparent resin, for example, epoxide resin and hermetically sealed.

In FIGS. 25 and 26 is shown a modified embodiment of the light emitting device shown in FIGS. 22 and 23. In the present embodiment, light emitting chips 106, 107, 108 emitting blue, green and red lights, respectively, and a circuit for driving these light emitting chips are incorporated into a semiconductor substrate 204 which is enclosed in the hermetically sealed package 101 shown in FIGS. 22 and 23. Conductors 206, 207, 208, 209, 210 led into the package 101 are connected through conductors 211, 212, 213, 214 each having a high electric conductivity (for example gold) to each terminal of the circuit (FIGS. 27 and 28) incorporated into the semiconductor substrate 204.

The use of one package enclosing therein a plurality of solid state light emitting chips and the circuit for driving these chips permits an extremely compact solid state light emitting device which is easy in handling and can be mounted as the light source in the endoscope in a simple manner.

In FIGS. 27 and 28 are shown two embodiments of the circuit for driving the light emitting chips and incorporated into the semiconductor substrate enclosed in the hermetically sealed package. In the present embodiments, photodiodes are used as the blue, green and red light emittin chips. In the embodiment shown in FIG. 27. NPN junction transistors are used as the driving transistors. Signal input terminals 215, 216, 217 connected through the conductors 211, 212, 213 to the lead wires 206, 207, 208 are connected through resistors 218, 219, 220 to base electrodes of the NPN junction driving transistors 221, 222, 223 whose collector electrodes are connected through resistors 224, 225, 226 to cathode electrodes of the blue, green, red light emitting photodiodes 201, 202, 203 whose anode electrodes and the emitter electrodes of the driving transistors 221, 222, 223 being connected in parallel between electric supply source terminals 227 and 228. One of the electric supply source terminals 227 is connected through the conductor 214 to the lead wire 209, while the other electric supply source terminal 228 is connected through a head for supporting the semiconductor substrate 204 to the lead wire 210.

In the present embodiment, a constant stabilized direct current supply source voltage is applied between the electric supply source terminals 227 and 228 and a driving input signal is supplied between signal input terminals 215, 216, 217 and one of the electric supply source terminals 228 in succession. The driving transistors 221, 222, 223 are switched on in succession in response to the driving input signals to cause the photodiodes 201, 202, 203 to emit light in succession.

In the embodiment shown in FIG. 28, PNP junction transistors are used as the driving transistors. Signal input terminals 215', 216' 217' are connected through resistors 218', 219', 220' to base electrodes of the PNP junction driving transistors 221', 222', 223' whose collector electrodes are connected through resistors 224', 225', 226' to anode electrode of blue, green, red light emitting photodiodes 201', 202', 203' whose cathode electrodes and the emitter electrodes of the driving transistors 221', 222', 223' being connected in parallel between electric supply source terminals 227' and 228'. In the present embodiment, a constant stabilized direct current supply source voltage is applied between the electric supply source terminals 227' and 228' and a driving input signal is supplied between signal input terminals 215', 216', 217' and one of the electric supply source terminals 228' in succession. The driving transistors 221', 222', 223' are switched on in succession in response to the driving input signals to cause the photodiodes 201', 202', 203' to emit light in succession.

As described above, the circuits shown in FIGS. 27 and 28 make it possible to use a minute current as the input signal for switching on the driving transistors 221, 222, 223 and 221', 222', 223'. As a result, it is sufficient to use conductors each having a diameter on the order of 0.3 to 0.4 mm as the conductors for connecting the external electric supply source circuit 121 (FIG. 24) to the signal input terminals 215, 216, 217 and 215', 216', 217'.

In FIG. 29 is shown an embodiment of the endoscope according to the invention which makes use of the solid state light emitting device 101' composed of the solid state light emitting device shown in FIGS. 25 and 26 and the circuit shown in FIG. 27 or FIG. 28. The circuit elements, arrangement and operation thereof are substantially the same as those described with reference to FIG. 24.

As in the embodiment shown in FIG. 24, in the present embodiment, both the external light source and the tricolor filter are not used and the successive operations of the solid state light emitting chips are synchronized with the picture image signal from an object to be visualized at the signal change-over circuit 28, thereby easily deriving the picked-up signals.

In addition, the solid state light emitting device comprises the driving circuit incorporated therein has the same advantages as those described with reference to the embodiment shown in FIGS. 22 and 23.

In FIG. 30 is shown a modified embodiment of the light decomposition optical system shown in FIG. 10. The light decomposition optical system shown in FIG. 30 is provided at its side surfaces with signal transfer wires and connector contacts. As in the light decomposition optical system shown in FIG. 10, the pentaprism 52 is provided at its image forming surface with the solid state image pick-up device 53 secured thereto. The image forming surface is provided at its both side edges with a number of contacts 308A, 308A'.

Those two side surfaces of the pentaprism 52 which are connected through the dichroic mirror 54 to the block 37 are provided at their two side edges with contacts 308B. 308C and signal transfer wires 309 connecting these contacts 308B, 308C to the contacts 308A, 308A', respectively. Each of the electrodes of the solid state image pick-up device 53 is connected to each of the contacts 308A, 308A'. In addition, the block 57 is provided at that end surface to which the solid state image pick-up device 59 is secured with a number of contacts 310A, 310A' arranged along both the side edges of the block 57. Each of these contacts 310A, 310A' is connected to each of the electrodes of the solid state image pick-up device 59. The block 57 is provided at its both side surfaces with contacts 310A, 310B and connector contacts 310B' arranged along both the side edges of the block 57, each of the contacts 310B being connected to each of the connector contacts 310B' by means of signal transfer wires 312. Each of the connector contacts 310B is connected to each of the contacts 310A. When the pentaprism 52 is abutted against the block 57, each of the contacts 308C is connected to each of the contacts 310B.

The above mentioned contacts 308, 310A, signal transfer wires 309, 312 and connector contacts 310B may simply be obtained by vapor deposition of a metal layer having a given pattern. The contacts 308C may be electrically connected to the contacts 310B by bonding, etc.

The same driving signal may be supplied through the conductor to the solid state image pick-up devices 53, 59 and the picture signals from these solid state image pick-up devices 53, 59 may be led through the above mentioned signal transfer wires and contacts provided on the side surfaces of the block 37 to the exterior circuit independently of the driving signal supplying conductor.

In FIG. 31 is shown one embodiment of a receptacle adapted to be joined to the connector contact plates 310B' shown in FIG. 30. The receptacle shown in FIG. 31 is of a frame-shaped one and is provided at its inner side wall surfaces with a number of receptacle contacts 314. When the receptacle 313 is fitted around the end portion of the block 57 shown in FIG. 30, each of the receptacle contacts 314 is connected to each of the connector contacts 310B' provided on the side surfaces of the block 57. The receptacle contacts 314 may be obtained by vapor deposition of a metal layer having a given pattern in the same manner as in the case of the above mentioned contacts. Each of the receptacle contacts 314 is connected through each of lead wires 315 to the external circuit of the endoscope.

As described above, all of the electrodes of the solid state image pick-up devices 53, 59 are connected through the contacts 308, 310 and the signal transfer wires 309, 312 to each of the connector contacts 310B' provided on the side walls of the end portions of the block 37, and as a result, the light decomposition optical system may easily be mounted in that part of the endoscope which is inserted into the hollow cavity by merely inserting the block 57 into the receptacle 313 previously secured to front end of the sheath 14 (FIG. 32).

In FIG. 32 is shown one embodiment of the endoscope according to the invention which comprises the sheath 14 including the above mentioned light decomposition optical system shown in FIGS. 30, 31 and the external circuit shown in FIG. 14. The operation of the present embodiment is substantially the same as that described with reference to FIG. 14.

In the present embodiment, the lead wires of the external circuit to be connected to the solid state image pick-up devices are not directly connected to the electrodes of the solid state image pick-up devices, but are connected to the receptacle contacts 314 of the receptacle 313 secured to the inner wall of the sheath 14, so that when the solid state image pick-up device or the light decomposition optical system becomes damaged, these device or system may easily be removed out of the sheath 14 with the lead wires remained in the sheath 14 as they were. In addition, that part of the endoscope which is inserted into the hollow cavity may be made small in size.

In FIG. 33 is shown one embodiment of the bundle of lead wires 6 connected to the solid state image pick-up devices 53, 59 and connected to the exterior circuit shown in FIG. 14, for example. The bundle of lead wires 6 is composed of picture image signal wires 415, 417 and driving compensation signal wires 416, 418 from the solid state image pick-up devices 53, 59 and connected to the amplifiers 132, 133 shown in FIGS. 14 and 33. In the present embodiment, the picture image signal wire 415 and the driving compensation signal wire 416 from the solid state image picking-up device 53 are twisted together along their overall length to form a stranded wire which is connected to the differential input terminals of the differential amplifier 132. Similarly, the picture image signal wire 417 and the driving compensation signal wire 418 are twisted together along their overall length to form a stranded wire which is connected to the differential input terminals of the differential amplifier 132.

As a result, in the picture image signal wires 415, 417, there are produced a picture image signal $v$ and noise $a$ produced due to all of the driving signals as shown in FIG. 34A, while in the driving compensation signal wires 416, 418, there are produced driving compensation signal $b$ produced due to all of the driving signal as shown in FIG. 34B. These signals are present whether or not the picture image signal wire and the driving compensation signal are twisted together. On the other hand, there is a risk of the exterior noise being mixed into the signal wires between the solid state image pick-up device and the differential amplifier. In the present embodiment, the signal wires are twisted together along their overall length, so that the exterior noise is equally produced in both the signals as shown by $c$ in FIG. 34A and $d$ in FIG. 34B. As a result, if both the signals shown in FIGS. 34A and 34B are subtracted one from the other in the differential amplifier 132, 133, it is possible to cancel not only the noise caused by the driving signal but also the external noise, thereby leading out a normal picture image output signal $v$ as shown in FIG. 34C.

In the prior art techniques, the signal wires are merely assembled together to form a bundle of lead wires. In this case, noise is included in either one of the signal wires. On the contrary, the present embodiment of twisting together the signal wires along their overall length is capable of equally mixing various noises into each of the signal wires and hence of producing the normal picture image signal without including no noises from the differential amplifiers 132, 133 in a simple manner. As a result, it is possible to display a distinct picture image inclusive of no color displacement nor ghost.

what is claimed is:

1. An endoscope for displaying a color picture image of an object to be viewed in a hollow cavity, comprising a sheath to be inserted into said hollow cavity and an exterior circuit arranged outside said sheath, said sheath including a self-scanning type solid state image pick-up device, a bundle of lead wires composed of a lead wire for supplying a signal for operating said image pick-up device from said exterior circuit and a lead wire for leading out a picture signal supplied from said image pick-up device toward said exterior circuit, and an illumination light transfer body comprised of flexible light-conducting fibers for transferring a light for illuminating said object to be viewed from said exterior circuit, said exterior circuit including a signal generator for operating said self-scanning type solid state image pick-up device, an amplifier for amplifying said picture signal supplied from said image pick-up device, a color picture tube for displaying a color picture image upon receipt of said picture image signal from said amplifier, a light source for emitting illumination light on said illumination light transfer body, means for decomposing light incident on said illumination flexible light-conducting fibers into three primary color lights and a signal change-over circuit for changing over a signal supplied to said picture tube by a synchronizing signal.

2. An endoscope according to claim 1 wherein said means for decomposing light incident on said illumination light transfer body into color lights is a rotary tricolor filter arranged between said light source and said illumination light transfer body.

3. An endoscope according to claim 1 wherein said means for decomposing light incident on said illumination light transfer body into color lights comprises a light decomposition optical system composed of a pentaprism, a dichloric mirror on one surface of said pentaprism and for reflecting a given color light and transmitting other color lights therethrough, a reflecting mirror on another surface of said pentarprism for reflecting again said given color light reflected by said dichroic mirror, said self-scanning type solid state image pick-up device comprising a first solid state image pick-up device on a further surface of said pentaprism for receiving the light reflected by said reflecting mirror and a second solid state image pick-up device for receiving the light transmitted through said dichloric mirror, either one of said solid state image pick-up devices being opposed to an optical filter for decomposing the light.

4. An endoscope according to claim 3 wherein said light decomposition optical system further comprises a light transmission block including said dichroic mirror on its one end surface and another dichroic mirror on another end surface of said block for decomposing the light transmitted through said dichroic mirror, said first solid state image pick-up device being secured to one surface of said block for receiving one color light reflected by said dichroic mirror, said second solid state image pick-up device being secured to another surface of said block for receiving two color lights transmitted through said dichroic mirror, said exterior circuit further including a delay circuit for delaying the output from one of said solid image pick-up devices for one horizontal scanning period and a memory for reversing the output from another solid state image pick-up device for one horizontal scanning period.

5. An endoscope according to claim 3 wherein said light decomposition optical system is composed of a light transmission prism and a light transmission block each comprising a solid state image pick-up device secured to each of said prism and block, said light decomposition optical system being provided at its side surfaces with a number of signal transfer wires and connector contacts, said connector contacts being detachably connected to a number of receptacle contacts provided on the inner surface of a receptacle, and said receptacle contacts being connected to a number of lead wires.

6. An endoscope according to claim 1 wherein said light source for emitting an illumination light on said illumination light transfer body is a solid state light emitting device comprising one package with at least a transparent light outlet portion and a plurality of solid state light emitting chips enclosed in said package for emitting blue, green and red lights.

7. An endoscope according to claim 6 wherein said package encloses therein a semiconductor substrate and a plurality of solid state light emitting chips for emitting blue, green and red lights and a circuit for driving said solid state light emitting chips, said chips and circuits being deposited on said semiconductor substrate.

8. An endoscope according to claim 1 wherein a picture image signal wire and a driving compensation signal wire connected to said solid state image pick-up device are twisted together along their overall length to form a stranded wire, said stranded wire being connected to a differential amplifier provided in said exterior circuit.

* * * * *

UNITED STATES PATENT AND TRADEMARK OFFICE
CERTIFICATE OF CORRECTION

PATENT NO. : 4,074,306
DATED : February 14, 1978
INVENTOR(S) : KAKINUMA ET AL.

It is certified that error appears in the above-identified patent and that said Letters Patent are hereby corrected as shown below:

After line 7    insert:

-- Foreign Application Priority Data

| July 28, 1975 | Japan | 91064/75 |
| October 31, 1975 | Japan | 130529/75 -- |

Signed and Sealed this

*Fifth* Day of *September 1978*

[SEAL]

*Attest:*

RUTH C. MASON    DONALD W. BANNER
*Attesting Officer*    *Commissioner of Patents and Trademarks*